United States Patent [19]

Steiner et al.

[11] Patent Number: 4,798,605

[45] Date of Patent: Jan. 17, 1989

[54] DEVICE FOR CONNECTING AND DRAINING A POUCH

[75] Inventors: Roland Steiner, Thun; Eugéne Van Meir, Fribourg, both of Switzerland

[73] Assignee: Nestec S.A., Vevey, Switzerland

[21] Appl. No.: 76,177

[22] Filed: Jul. 21, 1987

[30] Foreign Application Priority Data

Aug. 1, 1986 [EP] European Pat. Off. ........ 86110670.6

[51] Int. Cl.$^4$ .......... A61B 19/00

[52] U.S. Cl. .......... 604/411; 604/414; 222/83

[58] Field of Search .......... 604/411–414, 604/274; 222/81, 83; 141/329, 350

[56] References Cited

U.S. PATENT DOCUMENTS

| | | | |
|---|---|---|---|
| 1,248,251 | 11/1917 | Breaux | 222/81 |
| 2,817,372 | 12/1957 | Barr, Sr. et al. | 604/411 |
| 4,201,208 | 5/1980 | Cambio, Jr. | 604/411 |
| 4,257,535 | 3/1981 | Mellett | 222/83 |
| 4,432,765 | 2/1984 | Oscarsson | 604/411 |
| 4,469,249 | 9/1984 | Malpas et al. | 222/83 |
| 4,473,369 | 9/1984 | Lueders et al. | 604/411 |
| 4,493,438 | 1/1985 | Rutter | 222/83 |
| 4,567,999 | 2/1986 | Hjertman et al. | 604/411 |
| 4,606,734 | 8/1986 | Larkin et al. | 604/414 |
| 4,624,392 | 11/1986 | Malpas et al. | 222/83 |

*Primary Examiner*—John D. Yasko

*Attorney, Agent, or Firm*—Vogt & O'Donnell

[57] ABSTRACT

A device for continuously draining a pouch is adjustable for puncturing and draining the pouch. In certain embodiments, the device has an end portion capable of being affixed to a joint affixed to a pouch. An end-piece is connected with the affixing end portion by means for reciprocating the end-piece towards and away from the joint and pouch. A needle affixed to the end-piece extends towards the pipe and joint and has a length sufficient to penetrate through the joint to pierce the pouch when the end-piece is reciprocated towards the adjustable portion. A pipe is positioned relative to the end-piece for dispensing liquid flowing from a pierced pouch via the void from the joint to the end-piece. Alternatively, the reciprocation means is integral with and terminates in an end portion within which a pipe is affixed which is integral with a needle which has at least one opening communicating with a channel which communicates with the pipe for dispensing liquid flowing from the pouch into the void to the pipe via the needle opening and channel. Alternatively, a portion of an adjustable portion containing a needle and pipe circumscribes an extension pipe of a joint and defines a void therebetween. Means for reciprocating the adjustable portion and needle are positioned in the void. Additionally, alternatively, an adjustable portion is integral with a needle passing through it and into an extension pipe of the joint. Means to reciprocate the adjustable portion and needle are positioned in an annular void between the extension pipe and the portion of the adjustable portion which circumscribes the extension pipe.

7 Claims, 2 Drawing Sheets

DEVICE FOR CONNECTING AND DRAINING A POUCH

BACKGROUND OF THE INVENTION

The invention relates to a device for connecting and draining a pouch containing a liquid, which can be fitted on a joint integral with said pouch, in particular for enteral or parenteral feeding.

U.S. Pat. No. 3,685,795 relates to a collecting bag, in particular for blood, comprising a coupling system allowing said bag to be opened and closed at will so as to distribute some of the blood from the collecting bag to a second bag. This coupling system advantageously replaces a distributing valve and in no way relates to enteral or parenteral feeding.

Numerous joining devices for the enteral or parenteral feeding of patients are known. If the join is made at the base of the feeding bag, joints or pipes will have to be inserted into the actual bag, and this leads to defects in sealing which are absolutely unacceptable. Furthermore, the production of bags of this type, which end in a funnel shape and on which there are welded joints with pipes or tubes through which a needle has to be introduced, is very complicated and expensive. If the join is made on the side of the feeding bag, a needle which remains engaged in the bag during use and which risks perforating the opposite face during draining is usually used. Moreover, since the needle remains inside the bag, the bag cannot drain entirely.

SUMMARY OF THE INVENTION

The present invention provides the user with an absolutely safe device which is also economical, quick to use and of relatively simple design and which allows complete drainage of the product and use of a bag which is simple to make up.

The device according to the invention comprises a portion which can be adjusted to the joint integral with the pouch, a needle having an axis of symmetry substantially coinciding with that of the adjustable portion, a means for automatic or manual return of the needle into its starting position and a system for discharging the liquid.

The adjustable portion is rendered integral with the joint of the pouch by a screw system, a bayonet fitting, a catch, or by nesting, preferably using a system with an annular groove, on the joint and an annular bead on the adjustable portion or vice-versa. A perfectly watertight connecting system must be produced in each case.

The material used is a plasatics material suitable for use in the food industry which has good properties of elasticity, such as polyolefins, for example, polyethylene, natural elastomers such as rubber or synthetic elastomers such as silicones.

Thus, in a first embodiment, the device of the present invention is adjustable and is capable of being affixed to a joint affixed to a pouch containing liquid to be dispensed. An end portion is capable of being affixed to the joint. An end-piece is connected with the affixing end portion by means for allowing reciprocation of the end-piece in a direction towards and in a direction away from the affixing end portion. A void is defined by the end-piece, the reciprocation means, the affixing end portion and the joint for liquid from a pierced pouch to flow towards the end-piece. A needle is affixed to the end-piece and extends within the void. The needle is tapered to a point in a direction from the end-piece to the affixing end portion. The needle has a length such that when the end-piece is at a reciprocated position away from the affixing end portion, the point of the needle is displaced away from the pouch. The needle, however, has a length sufficient for penetrating through the joint for piercing the pouch when the end-piece is at a reciprocation position towards the affixing end portion. The needle has a diameter smaller than a diameter of the void for allowing liquid to flow through the void about the needle. A pipe is positioned between the end-piece and reciprocation means for dispensing liquid flowing from a pierced pouch towards the end-piece about the needle via the void.

In a second embodiment, the reciprocation means terminates in an end portion integral with the reciprocation means in lieu of a separate end portion. A pipe is affixed within the integral end portion and is integral with a needle. The needle, while having a diameter smaller than the void, has a diameter sufficient for accommodating at least one opening communicating with a channel which terminates at and communicates with a channel of the pipe for dispensing liquid flowing from a pierced pouch via the void to the needle opening and through the needle channel to the pipe.

In a third embodiment, the device has an adjustable portion which has a first portion defining a void through which a needle passes into an extension pipe of the joint. The needle has an opening and channel connected to a pipe passing out of the first portion of the adjustable portion for delivery of liquid from the extension pipe away from the adjustable portion. A second portion of the adjustable portion circumscribes the extension pipe, and abutments on the second portion and extension pipe define a void between them. Means to reciprocate the adjustable portion and needle are positioned in the void between the extension pipe and the second portion of the adjustable portion.

In a fourth embodiment, an adjustable portion contains an end-piece, needle and pipe, as in the first embodiment, and circumscribes an extension pipe of a joint and is reciprocated and then positioned with a system of grooves and beads.

DESCRIPTION OF PREFERRED EMBODIMENTS

According a first embodiment, the means allowing return of the needle is a bellows-type system arranged in the extension of the portion which can be adjusted to the joint. This bellows-type system comprises between 1 and 5 folds, preferably between 1 and 3 folds. The use of the device according to the invention will be explained with reference to the Figures.

According to a second embodiment, the means allowing return of the needle is a spring fitted in the portion which is adjusted to the joint. This spring is preferably a coil spring which is coaxial to the needle.

According to a third embodiment, the means allowing return of the needle is a system with a double annular groove on the exterior of the joint cooperating with a bead system in the internal portion of the portion which can be adjusted to the joint. It is also possible to provide two annular beads at the end of the joint and an annular groove on the adjustable portion.

With regard to discharge of the food product, this is effected either by a piping system outside the needle or by piping in the extension of the needle, said needle thus comprising at least one opening.

The needle can form an integral part of the device, or can be screwed, welded or mounted therein by a bead and an annular groove system or can be force-fitted.

An additional feeding tube for addition of vitamins or other substances into the basic food can also be provided on the device according to the invention.

The remainder of the description is given with reference to the drawing Figures.

DETAILED DESCRIPTION OF DRAWINGS

Figure 1:
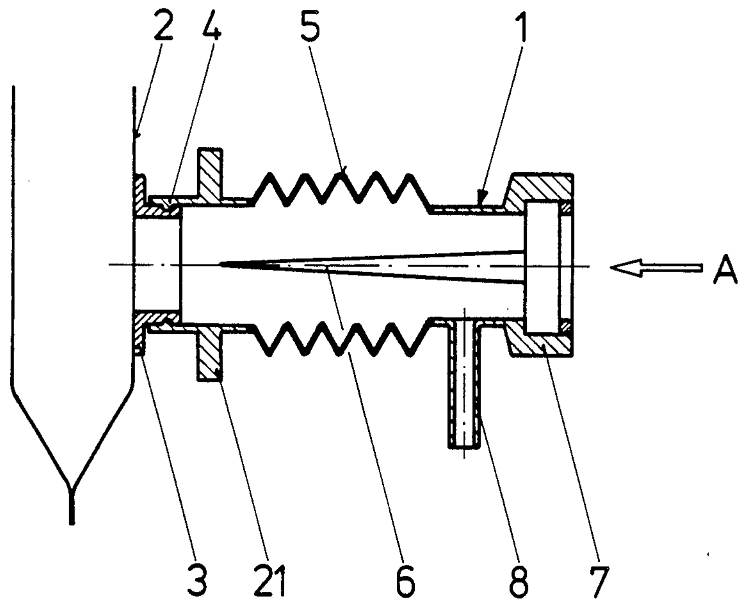
FIG. 1 is a schematic illustration of the device according to the invention according to the first embodiment.

In FIG. 1, the device (1) according to the invention is designed to be mounted on a bag (2) containing a liquid product, for example for enteral feeding. This bag is preferably a flexible plastic bag comprising a joint (3) with annular groove. The adjustable portion (4) of the device according to the invention comprises an annular bead for connecting the device (1) to the bag (2). The adjustable portion (4) comprises in its extension a flexible bellows-type system (5) with 5 folds. The needle (6) is coaxial with the portion (4) and the system (5) and is screwed on the end-piece (7). The pipe (8) can be connected to a flexible hose which is in turn connected to the patient to be fed.

The device according to the invention is operated in the following manner: The device (1) is mounted on the joint (3). A retaining member (21) is provided to prevent perforation of the bag during assembly of said device. The end-piece is pushed such as by a finger in the direction of the arrow A until the needle (6) perforates the wall of the bag (2). When the finger is removed, the needle (6) returns to its starting position owing to the particular design of the flexible system (5), the liquid is thus sucked out of the bag (2) and reaches the device round the needle and flows in the pipe (8) towards the patient to be fed. The length of the needle is such that it perforates one of the faces of the bag and not the other. It can therefore been seen that, according to the invention, one is provided with a system which can be manipulated without risk of error by the user and can be assembled on the feeding pouch within only a few seconds.

Figure 2:
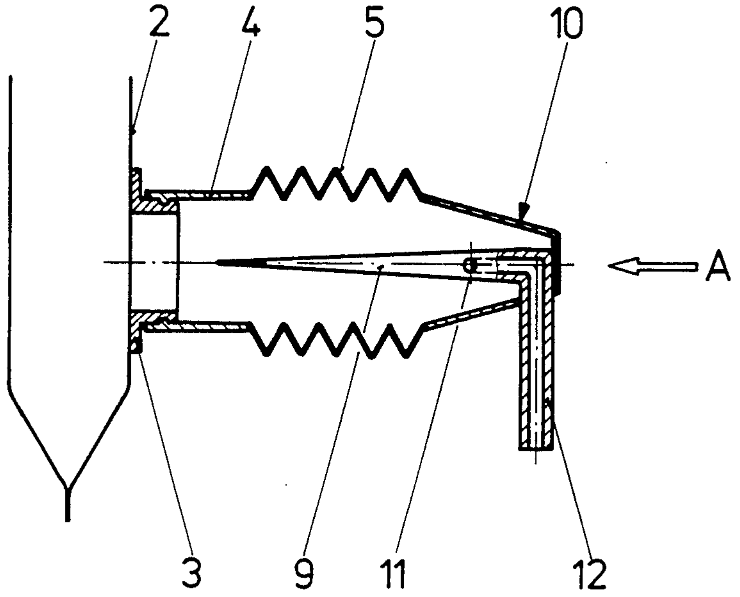
FIG. 2 is a variation of the first embodiment.

The same elements have been denoted by the same reference numerals in FIG. 2. The device (10) differs from FIG. 1 in that the needle (9) comprises an opening (11) through which the feeding liquid will flow towards the pipe (12). The principle of use remains the same as before, however.

Figure 3:
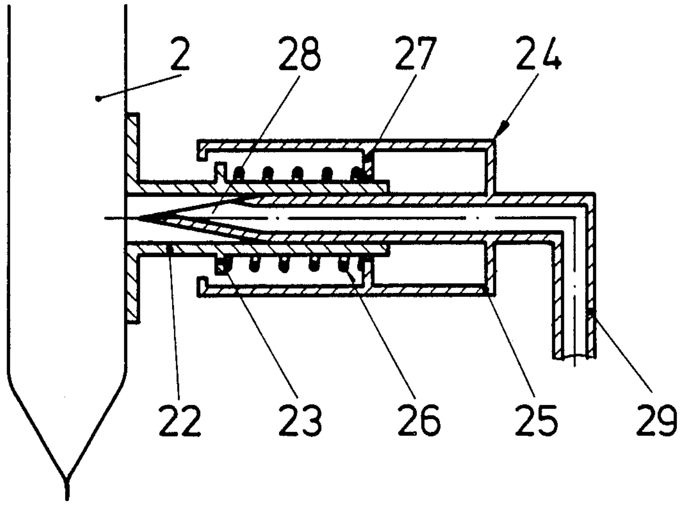
FIG. 3 is an illustration of the device according to the invention according to the second embodiment.

In the embodiment shown in FIG. 3, the bag (2) comprises a joint (22) with an annular abutment (23). The device according to the invention (24) is fitted on the joint (22). The adjustable portion (25) comprises a spring (26) and an abutment (27). The needle (29) comprises an opening (28). In this version, the seal is produced by the needle (29) inside the joint (22).

When the adjustable portion (25) is on the joint (22), the needle is pushed so that it perforates the bag (2). The spring (26) is compressed by resting on the abutments (23) and (27). When the bag is perforated, the needle is released and the device returns to its starting position by the force of reaction of the spring (26). The liquid flows through the opening (28) in the needle towards the patients to be fed.

Figure 4:
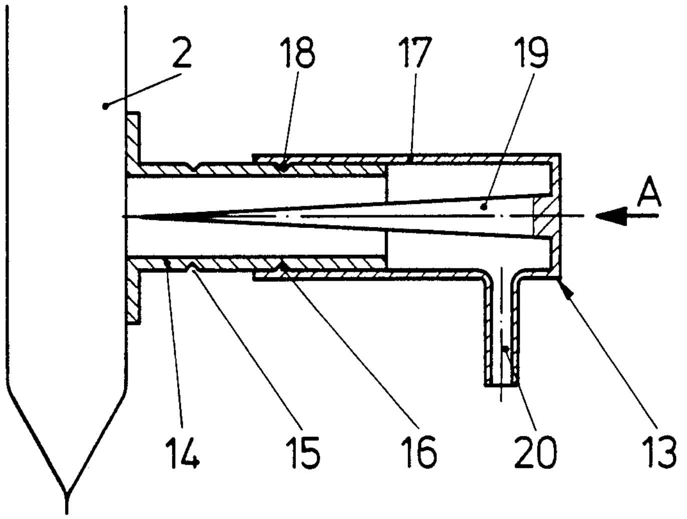
FIG. 4 is an illustration of the device according to the invention according to the third embodiment.

In the embodiment shown in FIG. 4, the bag (2) comprises a joint (14) with two annular grooves (15, 16). The device (13) according to the invention comprises an adjustable portion (17) with a circular bead (18), the needle (19) and the pipe (20). The following procedure is adopted: The device (13) is pushed in the direction of the arrow A until the bead (18) cooperates with the annular groove (15). The needle (19) thus perforates the wall of the bag (2) and the feeding liquid flows into the device. It is merely necessary to withdraw the device (13) into its starting position.

The device according to the invention is simple in design, practical in use, economical, fast, and allows complete drainage of the product on any type of pouch, in particular on a square or rectangular shaped bag. When packaged in sterile manner, it allows the risks of contamination during use to be minimized.

The device according to the invention can also be used for draining containers of liquids for drinks, in which case a valve is optionally provided at the end.

We claim:

1. A device which is adjustable and for being affixed to a joint affixed to a pouch containing liquid for continuously draining the pouch comprising:

an end-piece of the device displaced from an end portion of the device, the end portion being capable of being affixed to a joint affixed to a pouch containing liquid to be dispensed;

means connecting the end-piece with the affixing end portion for reciprocation of the end-piece in a direction towards and in a direction away from the affixing end portion, the end-piece, the reciprocation means, the affixing end portion and the joint defining a void for liquid from a pierced pouch to flow towards the end-piece;

a needle affixed to the end-piece and extending within the void, the needle being affixed to the end-piece for having an axis of symmetry substantially corresponding with an axis of symmetry of the void, being tapered to a point in a direction from the end-piece to the affixing end portion, having a length such that when the end-piece is at a reciprocated position away from the affixing end portion, the point of the needle is displaced away from the pouch but having a length sufficient for penetrating through the joint for piercing the pouch when the end-piece is at a reciprocated position towards the affixing end portion and having a diameter smaller than a diameter of the void; and a pipe positioned between the end-piece and the reciprocation means for dispensing liquid flowing from a pierced pouch via the void about the needle towards the end-piece.

2. A device which is adjustable and for being affixed to a joint affixed to a pouch containing liquid for continuously draining the pouch comprising:

an end portion of the device capable of being affixed to a joint affixed to a pouch containing liquid to be dispensed;

means connected with the affixing end portion and terminating in an integral end portion for allowing reciprocation of the integral end portion in a direction towards and in a direction away from the affixing end portion, a void being defined by the integral end portion, the reciprocation means, the affixing end portion and the joint for liquid from a pierced pouch to flow into and through the void towards the integral end portion; and a pipe affixed within the integral end portion for dispensing liquid and being integral with a needle extending within the void and being positioned by means of the affixed pipe for having an axis of symmetry substantially corresponding with an axis of symmetry of the void, being tapered in a direction from the integral end portion to the adjustable portion, having a length such that when the integral end portion is at a reciprocated position away from the affixing end portion, the point of the needle is displaced away from the pouch but having a length sufficient for penetrating the pouch when the integral end portion is reciprocated towards the affixing end portion and having a diameter smaller than a diameter of the void for liquid to flow into and through the void about the needle but sufficient for accommodating at least one opening communicating with a channel communicating with the affixed pipe for dispensing liquid flowing from a pierced pouch via the void to the needle opening and through the needle channel to the pipe.

3. A device according to claim 1 or 2 wherein the reciprocating means is a bellows-type system.

4. A device according to claim 3 wherein the bellows-type system has from 1 to 5 folds.

5. A device according to claim 3 wherein in that the material for the bellows-type system is selected from the group consisting of polyolefins, synthetic elastomers and natural elastomers.

6. A device which is adjustable and for being affixed to a joint affixed to a pouch containing liquid for continuously draining the pouch comprising:

a joint capable of being attached to a pouch and having an extension pipe which has a hollowed interior having two spaced apart annular grooves about its outer circumference;

an adjustable portion circumscribing the extension pipe capable of being reciprocated towards and away from the joint and pouch and having two spaced apart annular beads positioned for mating with the grooves of the extension pipe and having an end portion and a pipe spaced away, with respect to a direction away from the joint and pouch, from the position of the beads; and a needle affixed to the end portion of the adjustable portion having an axis of symmetry substantially corresponding with an axis of symmetry of the joint and extension pipe, and being tapered from the end portion to a point, being a size smaller than a void defined by the extension pipe and adjustable portion and having a length sufficient for piercing the pouch when the adjustable portion is reciprocated towards the pouch and all grooves and beads are mated for piercing the pouch and being removed from the pouch when the adjustable portion is reciprocated away from the pouch and only one groove and bead are mated for dispensing liquid through the extension pipe to the adjustable portion pipe about the needle.

7. A device which is adjustable and for being affixed to a joint affixed to a pouch for continuously draining the pouch comprising:

a joint capable of being attached to a pouch and having an extension pipe which has a hollowed interior;

a needle extending within the extension pipe of the joint having a body portion having a diameter substantially the same as a diameter of the interior of the pipe for sealing the pipe and then being tapered to a point, there being at least one opening in the tapered portion communicating with a channel within the needle;

an adjustable portion having an annular abutment circumscribing the extension pipe defining a first portion which is affixed about the needle at a point displaced from the pipe and defining a void about the needle through which the needle extends to the extension pipe and a second portion circumscribing the extension pipe defining a second void about the extension pipe;

an annular abutment about the extension pipe spaced away from the adjustable portion abutment towards the joint and pouch; and a spring positioned between the extension pipe and adjustable portion abutments for reciprocating the adjustable portion, wherein the abutments are spaced sufficiently apart and the needle extends for a length sufficient from the adjustable portion and within the extension pipe such that when the adjustable portion and needle are pushed towards a pouch, the needle is capable of piercing the pouch, whereby upon reciprocation to its original position liquid flows into and through the channel of the needle for dispensing.

* * * * *

UNITED STATES PATENT AND TRADEMARK OFFICE

CERTIFICATE OF CORRECTION

PATENT NO. : 4,798,605

DATED : Jan. 17, 1989

INVENTOR(S) : Roland STEINER, et al.

It is certified that error appears in the above-identified patent and that said Letters Patent is hereby corrected as shown below:

Column 1, line 51, "plasatics" should be --plastics--.

Column 2, line 16, "in lieu" should be italicized.

Column 4, line 4, "patients" should be --patient--.

Signed and Sealed this

Thirteenth Day of June, 1989

*Attest:*

DONALD J. QUIGG

*Attesting Officer*

*Commissioner of Patents and Trademarks*